(12) United States Patent
Green, II et al.

(10) Patent No.: US 12,403,010 B2
(45) Date of Patent: Sep. 2, 2025

(54) KNEE REPLACEMENT IMPLANT HAVING STACKABLE SPACERS

(71) Applicant: Encore Medical, LP, Austin, TX (US)

(72) Inventors: John M. Green, II, Leander, TX (US); Laura Small, Austin, TX (US)

(73) Assignee: Encore Medical, LP, Austin, TX (US)

( * ) Notice: Subject to any disclaimer, the term of this patent is extended or adjusted under 35 U.S.C. 154(b) by 863 days.

(21) Appl. No.: 17/537,256

(22) Filed: Nov. 29, 2021

(65) Prior Publication Data

US 2022/0168111 A1     Jun. 2, 2022

Related U.S. Application Data

(60) Provisional application No. 63/119,802, filed on Dec. 1, 2020.

(51) Int. Cl.
    *A61F 2/38*          (2006.01)
    *A61F 2/30*          (2006.01)

(52) U.S. Cl.
    CPC .............. *A61F 2/3859* (2013.01); *A61F 2/385* (2013.01); *A61F 2002/30599* (2013.01); *A61F 2/389* (2013.01)

(58) Field of Classification Search
    CPC .......... A61F 2/3859; A61F 2002/30599; A61F 2002/30151; A61F 2002/30158; A61F 2/38; A61F 2/40; A61F 2/4081
    See application file for complete search history.

(56) References Cited

U.S. PATENT DOCUMENTS

| | | |
|---|---|---|
| 5,609,645 A | 3/1997 | Vinciguerra |
| 5,702,464 A | 12/1997 | Lackey et al. |

(Continued)

FOREIGN PATENT DOCUMENTS

| | | |
|---|---|---|
| EP | 2651343 B1 | 10/2013 |
| EP | 2822508 B1 | 1/2015 |

(Continued)

OTHER PUBLICATIONS

Examination Report mailed on Apr. 22, 2024 in AU 2021391408.

(Continued)

*Primary Examiner* — Sarah W Aleman
(74) *Attorney, Agent, or Firm* — Eversheds Sutherland (US) LLP

(57) ABSTRACT

A knee replacement prosthesis includes a distal femoral implant, including a femoral head portion, including an outer arcuate surface, and interior posterior surface, an interior distal surface disposed at a first angle with respect to the interior posterior surface, and a first interior intermediate surface joining the interior posterior surface and the interior distal surface and being disposed at a second angle with respect to the interior posterior surface and at a third angle with respect to the interior distal surface. The distal femoral implant includes stackable femoral spacers secured to at least one of the interior posterior surface and the interior distal surface, thereby adjusting an aggregate spacing between the interior posterior surface and/or the interior distal surface and a resected surface of a distal femur of the patient. A tibial implant is also provided. Related methods of use of either implant or both are also provided.

16 Claims, 10 Drawing Sheets

(56) References Cited

U.S. PATENT DOCUMENTS

| | | | |
|---|---|---|---|
| 5,755,800 A * | 5/1998 | O'Neil | A61F 2/30734 623/20.16 |
| 5,984,969 A | 11/1999 | Matthews et al. | |
| 6,074,424 A | 6/2000 | Perrone, Jr. et al. | |
| 7,892,288 B2 | 2/2011 | Blaylock et al. | |
| 8,167,888 B2 | 5/2012 | Steffensmeier | |
| 8,506,645 B2 | 8/2013 | Blaylock et al. | |
| 8,603,101 B2 | 12/2013 | Claypool et al. | |
| 8,632,599 B1 | 1/2014 | Bonitati et al. | |
| 8,968,413 B2 | 3/2015 | Cook et al. | |
| 9,011,459 B2 | 4/2015 | Claypool et al. | |
| 9,044,326 B2 | 6/2015 | Blaylock et al. | |
| 9,144,495 B2 | 9/2015 | Lin et al. | |
| 9,149,206 B2 | 10/2015 | Claypool et al. | |
| 9,265,614 B2 | 2/2016 | Blaylock et al. | |
| 9,427,337 B2 | 8/2016 | Claypool et al. | |
| 9,468,531 B2 | 10/2016 | Cook et al. | |
| 9,532,879 B2 | 1/2017 | Lieberman et al. | |
| 9,592,133 B2 | 3/2017 | Toler et al. | |
| 9,597,090 B2 | 3/2017 | Claypool et al. | |
| 9,763,807 B2 | 9/2017 | Claypool et al. | |
| 9,901,331 B2 | 2/2018 | Toler et al. | |
| 9,907,664 B2 | 3/2018 | Blaylock et al. | |
| 9,918,845 B2 | 3/2018 | Roby et al. | |
| 10,010,330 B2 | 7/2018 | Claypool et al. | |
| 10,052,207 B2 | 8/2018 | Chernosky et al. | |
| 10,085,841 B2 | 10/2018 | Blaylock et al. | |
| 10,188,530 B2 | 1/2019 | Claypool et al. | |
| 2004/0122521 A1 | 6/2004 | Lee et al. | |
| 2008/0051908 A1 | 2/2008 | Angibaud et al. | |
| 2008/0167722 A1 | 7/2008 | Metzger et al. | |
| 2012/0185053 A1 | 7/2012 | Berger | |
| 2012/0209391 A1 | 8/2012 | Cipolletti et al. | |
| 2013/0013077 A1 * | 1/2013 | Metzger | A61F 2/3859 623/20.35 |
| 2013/0079671 A1 | 3/2013 | Stein et al. | |
| 2014/0222155 A1 | 8/2014 | Metzger et al. | |
| 2016/0278925 A1 | 9/2016 | Roby et al. | |
| 2017/0333194 A1 | 11/2017 | Pierce et al. | |
| 2018/0098856 A1 | 4/2018 | Blaylock et al. | |
| 2019/0000632 A1 | 1/2019 | Blaylock et al. | |

FOREIGN PATENT DOCUMENTS

| | | |
|---|---|---|
| EP | 2830543 B1 | 2/2015 |
| EP | 2682073 B1 | 4/2015 |
| EP | 2710980 B1 | 7/2015 |
| EP | 2918235 B1 | 9/2015 |
| EP | 2921141 A2 | 11/2015 |
| EP | 2953583 B1 | 12/2015 |
| EP | 2777619 B1 | 8/2016 |
| EP | 3071152 A1 | 9/2016 |
| EP | 3335674 A2 | 1/2020 |
| FR | 3057760 A1 | 4/2018 |
| JP | 2014180559 A | 9/2014 |
| WO | 9730661 A1 | 8/1997 |
| WO | 2020093100 A1 | 5/2020 |

OTHER PUBLICATIONS

International Preliminary Report on Patentability received for WO Patent Application Serial No. PCT/US21/061017 dated Jun. 15, 2023, 10 pages.
Office Action mailed on Mar. 26, 2024 in JP 2023-533220.
Examination report No. 2 mailed on Jul. 9, 2024 in AU 2021391408.
Office Action mailed on Jul. 2, 2024 in JP 2023-533220.
Office Action mailed on Sep. 9, 2024 in CA 3198140.

* cited by examiner

KNEE REPLACEMENT IMPLANT HAVING STACKABLE SPACERS

CROSS REFERENCE TO RELATED APPLICATIONS

This application claims the benefit of U.S. Provisional Application No. 63/119,802, which was filed on Dec. 1, 2020, and the contents of which are incorporated by reference herein in its entirety.

BACKGROUND

Partial and/or total knee arthroplasty are commonly used to relieve pain and to correct mobility issues related to, and/or resulting from, degradation of one or more portions of one or both of a tibia and a distal femur within a patient's knee. However, as cost constraints become more prevalent, implant solutions that minimize inventory are becoming more important factors in the design and selection for use of such implant solutions. Accordingly, there is a need for providing implant solutions that minimize inventory and cost in both manufacture and use, while expanding the ability to accommodate more variability in the knees of prospective patients.

It should be noted that this Background is not intended to be an aid in determining the scope of the claimed subject matter nor be viewed as limiting the claimed subject matter to implementations that solve any or all of the disadvantages or problems presented above. The discussion of any technology, documents, or references in this Background section should not be interpreted as an admission that the material described is prior art to any of the subject matter claimed herein.

SUMMARY

In one implementation, a knee replacement prosthesis for a patient is provided. The prosthesis includes a tibial baseplate implant. The tibial baseplate implant includes a tibial baseplate including an upper surface and an underside. The tibial baseplate implant includes a plurality of stackable tibial spacers configured to be stacked directly on top of one another and secured directly to the underside of the tibial baseplate, thereby adjusting an aggregate spacing between the underside of the tibial base plate and a resected surface of a proximal tibia of the patient.

In another implementation, another knee replacement prosthesis for a patient is provided. The prosthesis includes a distal femoral implant. The distal femoral implant includes a femoral head portion. The femoral head portion includes an outer arcuate surface configured to mate with one of a tibial baseplate or a proximal surface of a tibia of the patient. The femoral head portion includes an interior posterior surface. The femoral head portion includes an interior distal surface disposed at a first angle with respect to the interior posterior surface. The femoral head portion includes a first interior intermediate surface joining the interior posterior surface and the interior distal surface such that the first interior intermediate surface is disposed at a second angle with respect to the interior posterior surface and at a third angle with respect to the interior distal surface. The distal femoral implant includes a plurality of stackable femoral spacers configured to be secured to at least one of the interior posterior surface and the interior distal surface, thereby adjusting an aggregate spacing between the at least one of the interior posterior surface or the interior distal surface and a resected surface of a distal femur of the patient.

In yet another implementation, a method of using a knee replacement prosthesis for replacing at least a portion of a knee of a patient is provided. The method includes resecting a proximal portion of a tibia of the patient to form a resected surface of the tibia. The method includes stacking a plurality of stackable tibial spacers directly on top of one another. The method includes securing the plurality of stackable tibial spacers directly to an underside of a tibial baseplate of a tibial baseplate implant. The method includes securing the tibial baseplate implant to the resected portion of the tibia, thereby providing a desired aggregate spacing between the underside of the tibial baseplate and the resected surface of the tibia.

In yet another implementation, another method of using a knee replacement prosthesis for replacing at least a portion of a knee of a patient is provided. The method includes resecting a distal portion of a femur of the patient to form a resected surface of the femur. The method includes stacking a plurality of stackable femoral spacers. The method includes securing the plurality of stackable femoral spacers to at least one of an interior posterior surface and an interior distal surface of a femoral head portion of a distal femoral implant. The interior distal surface is disposed at a first angle with respect to the interior posterior surface. The femoral head portion further includes an outer arcuate surface configured to mate with one of a tibial baseplate or a proximal surface of a tibia of the patient, and a first interior intermediate surface joining the interior posterior surface and the interior distal surface such that the first interior intermediate surface is disposed at a second angle with respect to the interior posterior surface and at a third angle with respect to the interior distal surface. The method includes securing the distal femoral implant to the resected surface of the femur, thereby providing a desired aggregate spacing between the at least one of the interior posterior surface or the interior distal surface of the femoral head portion and the resected surface of the femur.

It is understood that various configurations of the subject technology will become apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

Various embodiments are discussed in detail in conjunction with the Figures described below, with an emphasis on highlighting the advantageous features. These embodiments are for illustrative purposes only and any scale that may be illustrated therein does not limit the scope of the technology disclosed. These drawings include the following figures, in which like numerals indicate like parts.

DETAILED DESCRIPTION

The following description and examples illustrate some exemplary implementations, embodiments, and arrangements of the disclosed invention in detail. Those of skill in the art will recognize that there are numerous variations and modifications of this invention that are encompassed by its scope. Accordingly, the description of a certain example embodiments should not be deemed to limit the scope of the present invention.

Implementations of the technology described herein are directed generally to implants for use in partial or total knee arthroplasty. The apparatuses, systems and/or methods described herein simultaneously solve multiple problems, at least in part, by reducing a number of components of an implant or implant system while, counterintuitive, accommodating increased variability in anatomical characteristics of one or both knees of a wide range of candidate patients for partial or total knee arthroplasty.

Several embodiments of a knee replacement implant having one or more stackable spacers according to this disclosure will now be described in connection with FIGS. 1-6. Within this disclosure, such stackable spacers may also be known as, or called "augments." Discussion will first turn to embodiments of a tibial baseplate implant 100, as described in connection with at least FIG. 1 below.

Figure 1:
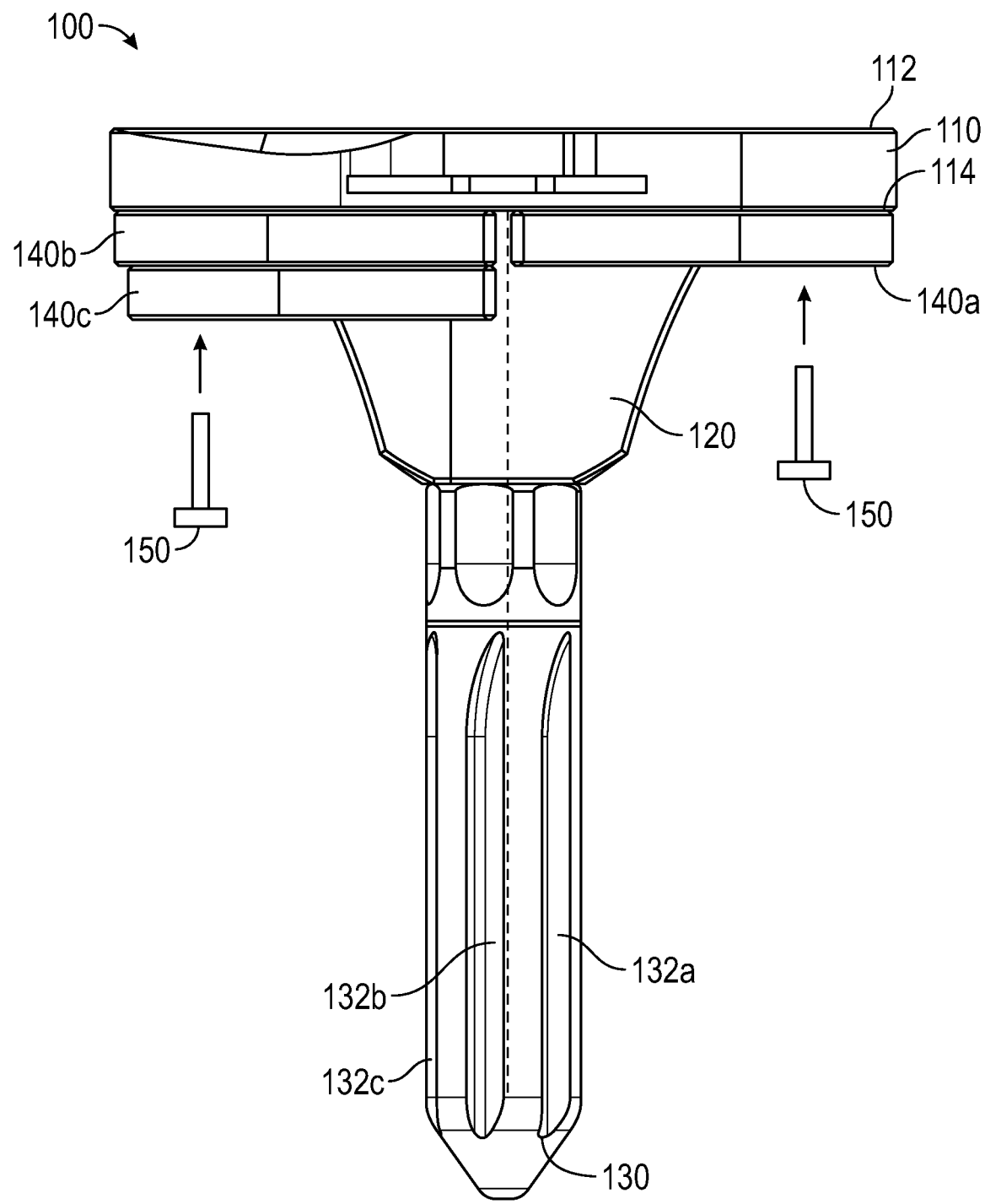
FIG. 1 shows a side view of tibial baseplate implant, in accordance with some embodiments.

FIG. 1 shows a side view of a tibial baseplate implant 100, in accordance with some embodiments. Tibial baseplate implant 100 can include a tibial baseplate 110 having an upper surface 112 configured to be disposed against at least one of a distal femur implant (as will be described in more detail below) or a distal femur within a patient's knee, and an underside 114 configured to receive one or more stackable tibial spacers 140a-140c. Tibial baseplate 110 further comprises a distal transitional portion 120 coupled to, couplable to, or monolithically integrated with underside 114 of tibial baseplate 110 at a proximal portion of distal transitional portion 120, and a stem 130 coupled to, couplable to, or monolithically integrated with a distal portion of distal transitional portion 120.

Stem 130 is configured to be disposed longitudinally into and secured within a cavity of a tibia of a patient. In some embodiments, stem 130 has a substantially cylindrical shape and a distal end that tapers to a point or substantially rounded point. However, stem 130 can have any suitable shape. In some embodiments, stem 130 comprises one or more longitudinal grooves or fluted or recessed portions 132a, 132b, 132c. In some embodiments, such grooves or fluted or recessed portions 132a, 132b, 132c may increase adhesion of stem 130 to inner surfaces of the tibia of the patient.

As illustrated, in some embodiments, distal transitional portion 120 may have a shape that generally tapers from its proximal end nearest underside 114 of tibial baseplate 110 toward its distal end nearest stem 130. In some embodiments, distal transitional portion 120 can comprise one or more fins, protrusions or protrusive portions that extend laterally away from distal transitional portion 120. Such fins, protrusions or protrusive portions may aid adhesion of distal transitional portion 120 to a surface of the tibia of the patient. In some embodiments, such fins, protrusions or protrusive portions may additionally or alternatively aid in the securing and/or aligning of one or more stackable tibial spacers 140a, 140b, 140c to underside 114 of tibial baseplate 110, as will be described below.

Tibial baseplate implant 100 may further comprise one or more stackable spacers 140a-140c. In some embodiments, one or more of stackable spacers 140a-140c (e.g., spacers 140a and 140b as illustrated) are configured to be secured directly to underside 114 of tibial baseplate 110 by one or more screws 250. In some embodiments, one or more of stackable spacers 140a-140c (e.g., spacers 140b and 140c as illustrated) are configured to be stacked directly on top of one another and secured to underside 114 of tibial baseplate 110 by one or more screws 250.

In some embodiments, spacers 140a-140c all have a same form factor, size or radius along their perimeters. In some embodiments, one or more of spacers 140a-140c have a different form factor, size or radius along its perimeter compared to one or more other of spacers 140a-140c. In some embodiments, spacers 140a-140c have a substantially circular, doughnut-shaped (e.g., substantially circular and having an aperture or opening configured to receive a portion of distal transition portion 120), or semicircular form factor such that they fit around and/or adjacent to at least a portion of distal transitional portion 120 and/or of stem 130. However, spacers 140a-140c may have any suitable form factor or shape.

In some embodiments, opposing stackable surfaces of each of spacers 140a-140c are substantially planar and parallel to one another such that, when stacked, negligible or no open space is present between mating stackable surfaces of adjacently stacked spacers.

In some embodiments, spacers 140a-140c all have a same thickness (e.g., 5 mm, although any suitable thickness is also contemplated). In some embodiments, one or more of spacers 140a-140c have a different thickness (e.g., 7 mm, 8 mm or 10 mm, although any other suitable thickness is also contemplated) from one or more other of spacers 140a-140c. By stacking one or more spacers 140a-140c having the same or different thicknesses, a greater variety of aggregate spacings between underside 114 of tibial baseplate 110 and a resected surface of a tibia of the patient can be obtained compared to systems in which spacers having same or different thicknesses are not specifically designed or configured to be so stacked. Moreover, stacking spacers 140a-140c allows for a smaller number of spacers to be utilized or inventoried while still providing an increased number of possible aggregate spacings at a lower cost of manufacture, use and/or inventory than is possible with other implant systems in which spacers are not specifically designed or configured to be so stacked.

Knee replacement prostheses according to the present disclosure can further or alternatively include a distal femoral implant 200 and one or more stackable femoral spacers 242a, 242b, 244a, 244b, 248a, 248b, 249a, 249b as will be described in more detail below. Discussion now turns to embodiments of distal femoral implant 200, as described in connection with at least FIGS. 2-5 below.

Figure 2:
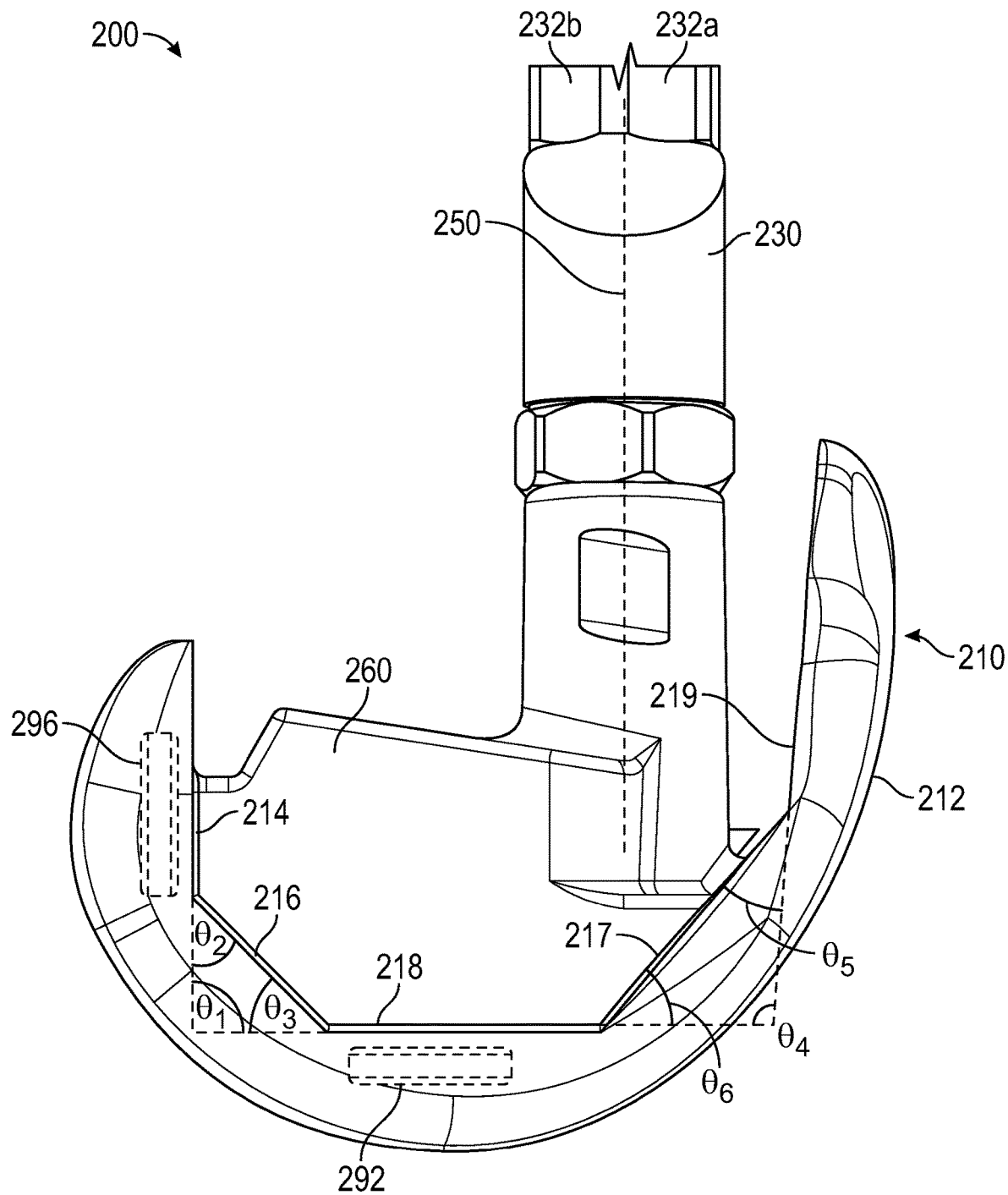
FIG. 2 shows a partial cutaway view of a distal femoral implant, in accordance with some embodiments.

FIG. 2 shows a partial cutaway view of distal femoral implant 200, in accordance with some embodiments. Distal femoral implant 200 comprises a femoral head portion 210 and a stem 230 coupled to, couplable to, or monolithically integrated with femoral head portion 210.

Stem 230 is configured to be disposed longitudinally into and secured within a cavity of a femur of a patient. In some embodiments, stem 230 has a substantially cylindrical shape. However, stem 230 can have any suitable shape. In some embodiments, stem 230 comprises one or more longitudinal grooves or fluted or recessed portions 232a, 232b. In some embodiments, such grooves or fluted or recessed portions 232a, 232b may increase adhesion of stem 230 to the inner surfaces of the femur of the patient. A longitudinal direction of extension of stem 230 is illustrated by dotted line 250 in FIG. 2.

Femoral head portion 210 comprises an outer arcuate surface 212 configured to mate with at least one of upper surface 112 of tibial baseplate 110 (see, e.g., FIG. 1) or a proximal surface of a tibia of the patient. Distal femoral implant 200 further comprises an interior posterior surface 214, an interior distal surface 218 disposed at a first angle ($\theta_1$) with respect to interior posterior surface 214, and an interior intermediate surface 216 joining interior posterior surface 214 and interior distal surface 218. The interior intermediate surface is disposed at a second angle ($\theta_2$) with respect to interior posterior surface 214 and at a third angle ($\theta_3$) with respect to interior distal surface 218. In some embodiments, the first angle ($\theta_1$) is substantially 90°. In some but not necessarily all such embodiments, interior posterior surface 214 may be substantially parallel to longitudinal direction of extension 250 of stem 230 and interior distal surface 218 may be substantially perpendicular to longitudinal direction of extension 250 of stem 230. However, any suitable first angle ($\theta_1$) and relative orientation(s) of interior posterior surface 214 and interior distal surface 218 are also contemplated.

In some embodiments, the second angle ($\theta_2$) between interior posterior surface 214 and interior intermediate surface 216 is substantially 45°. In such embodiments, where the first angle ($\theta_1$) is also 90°, the third angle ($\theta_3$) between interior intermediate surface 216 and interior distal surface 218 is also substantially 45° (i.e., second and third angles $\theta_2$, $\theta_3$ are substantially equal). Such 90°, 45°, 45° embodiments provide a unique advantage, as will be described in more detail below in connection with FIGS. 3A-3D and 4, in that spacers 242a, 242b, 244a, 244b and/or spacers 248a, 248b, 249a, 249b having beveled edges with a similar 45° angle can be stacked maximally close to one another, with negligible or no spacing between adjacent mating edges of the spacers, and in completely interchangeable, flipped (e.g., mirrored) orientations against each of interior posterior, intermediate and distal surfaces 214, 216, 218. However, any suitable second and third angles ($\theta_2$ and $\theta_3$) are also contemplated. Though, since first, second and third angles ($\theta_1$, $\theta_2$, $\theta_3$) form a triangle, their sum will add to 180°.

In some embodiments, distal femoral implant 200 further comprises an interior anterior surface 219 and a second interior intermediate surface 217 joining interior distal surface 218 and interior anterior surface 219. In some embodiments, interior anterior surface 219 is disposed at a fourth angle ($\theta_4$) with respect to interior distal surface 218. Second interior intermediate surface 217 is disposed at a fifth angle ($\theta_5$) with respect to interior anterior surface 219 and at a sixth angle ($\theta_6$) with respect to interior distal surface 218. In some embodiments, as illustrated in FIG. 2, the fourth angle ($\theta_4$) is slightly greater than 90°. Accordingly, in some but not necessarily all such embodiments, interior anterior surface 219 may extend slightly laterally and away from longitudinal direction of extension 250 of stem 230 when followed from distal to proximal edge. Fourth angle ($\theta_4$) being slightly greater than 90° has a benefit of increasing a size of a distal opening of an interior cavity of distal femoral implant 200 in which all above-mentioned interior surfaces 214, 216 and 217-219 are at least partly disposed, for more easily receiving a resected portion of a femur of the patient. However, any suitable fourth angle ($\theta_4$) is also contemplated.

In some embodiments, the fifth angle ($\theta_5$) between second interior intermediate surface 217 and interior anterior surface 219 is less than 45° and the sixth angle ($\theta_6$) between interior distal surface 218 and second interior intermediate surface 217 is substantially 45° (i.e., second, third and sixth angles $\theta_2$, $\theta_3$, $\theta_6$ are substantially equal). Embodiments where the sixth angle ($\theta_6$) is also 45° further supports the unique advantage that spacers 242a, 242b, 244a, 244b and/or 248a, 248b, 249a, 249b having beveled edges with a similar 45° angle, can be stacked maximally close to one another, with negligible or no spacing between adjacent mating edges of the spacers, and in completely interchangeable, flipped (e.g., mirrored) orientations against each of interior posterior, first and second intermediate and distal surfaces 214, 216-218. However, any suitable fifth and sixth angles ($\theta_5$ and $\theta_6$) are also contemplated. Though, since fourth, fifth and sixth angles ($\theta_4$, $\theta_5$, $\theta_6$) form a triangle, their sum will also add to 180°.

In some embodiments, one, some or all of interior posterior surface 214, interior intermediate surface 216, interior distal surface 218, second interior intermediate surface 217 and interior anterior surface 219 are substantially planar.

In some embodiments, distal femoral implant 200 comprises a median (or central dividing portion) 260 disposed substantially centrally therein. In some embodiments, stem 230 couples to, is couplable to, or is monolithically integrated with femoral head portion 210 at median 260. In some embodiments, a first portion of one or more of interior posterior surface 214, interior intermediate surface 216, interior distal surface 218, second interior intermediate surface 217 and interior anterior surface 219 are disposed to a first side of median 260 and a second portion of one or more of interior posterior surface 214, interior intermediate surface 216, interior distal surface 218, second interior intermediate surface 217 and interior anterior surface 219 are disposed to a second side of median 260 opposite the first side. Accordingly, all previously described angles between meeting surfaces of distal femoral head portion 210 (e.g., $\theta_1$, $\theta_2$, $\theta_3$, $\theta_4$, $\theta_5$, $\theta_6$) may have the same characteristics at each of the first and second portions of each of those meeting surfaces to either side of median 260.

As illustrated in FIG. 2, distal femoral implant 200 may further comprise at least one threaded aperture 292 configured to secure one or more stackable spacers to interior distal surface 218 utilizing a fastener 250, which in some embodiments may be a threaded screw. FIG. 2 also illustrates distal femoral implant 200 to further comprise at least one threaded aperture 296 configured to secure one or more stackable spacers to interior posterior surface 214 utilizing a fastener 250, which in some embodiments may be a threaded screw.

Figure 3A:
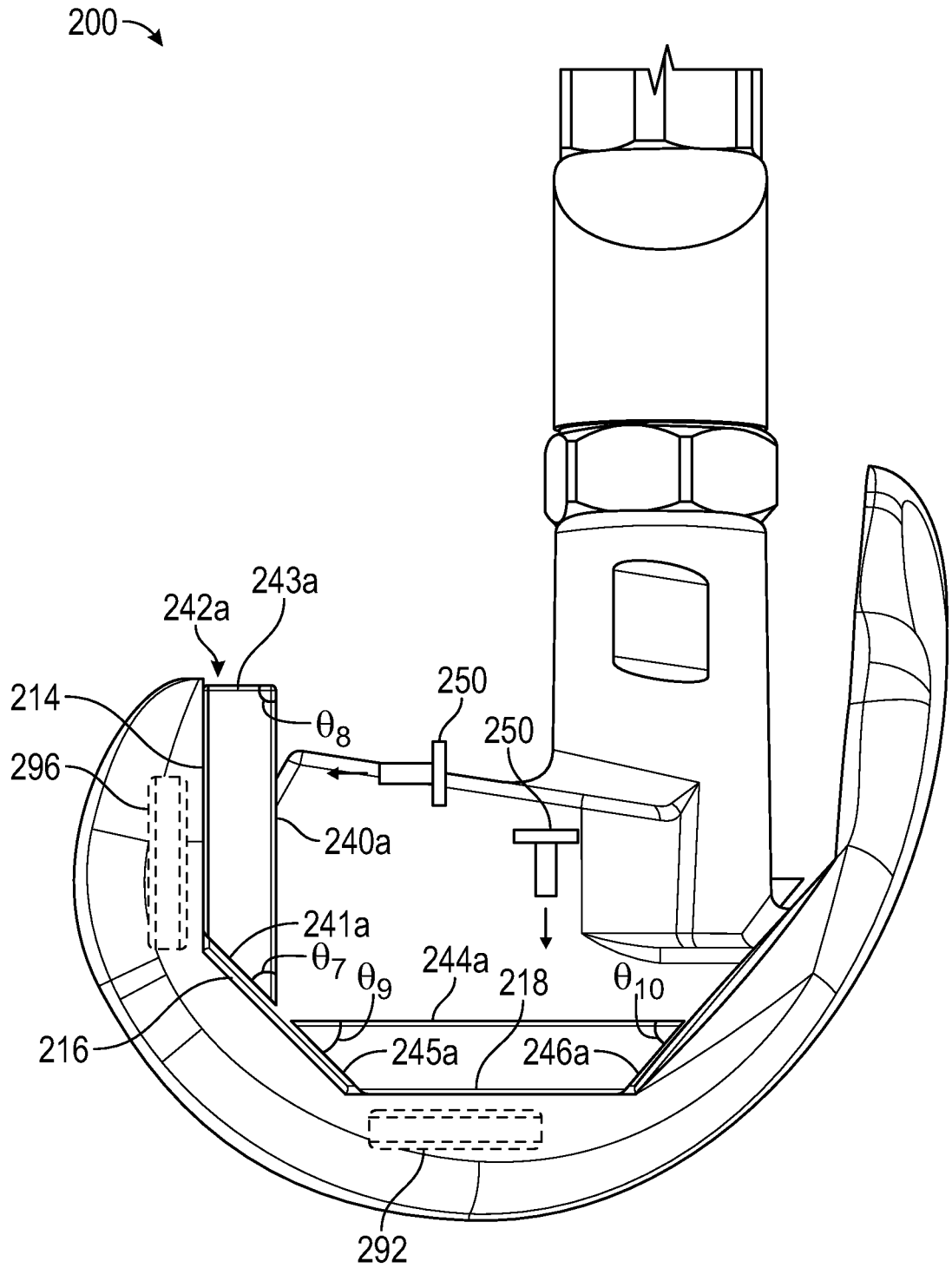
FIG. 3A shows a partial cutaway view of the distal femoral implant of FIG. 2 including one or more spacers disposed therein, in accordance with some embodiments.
Figure 3B:
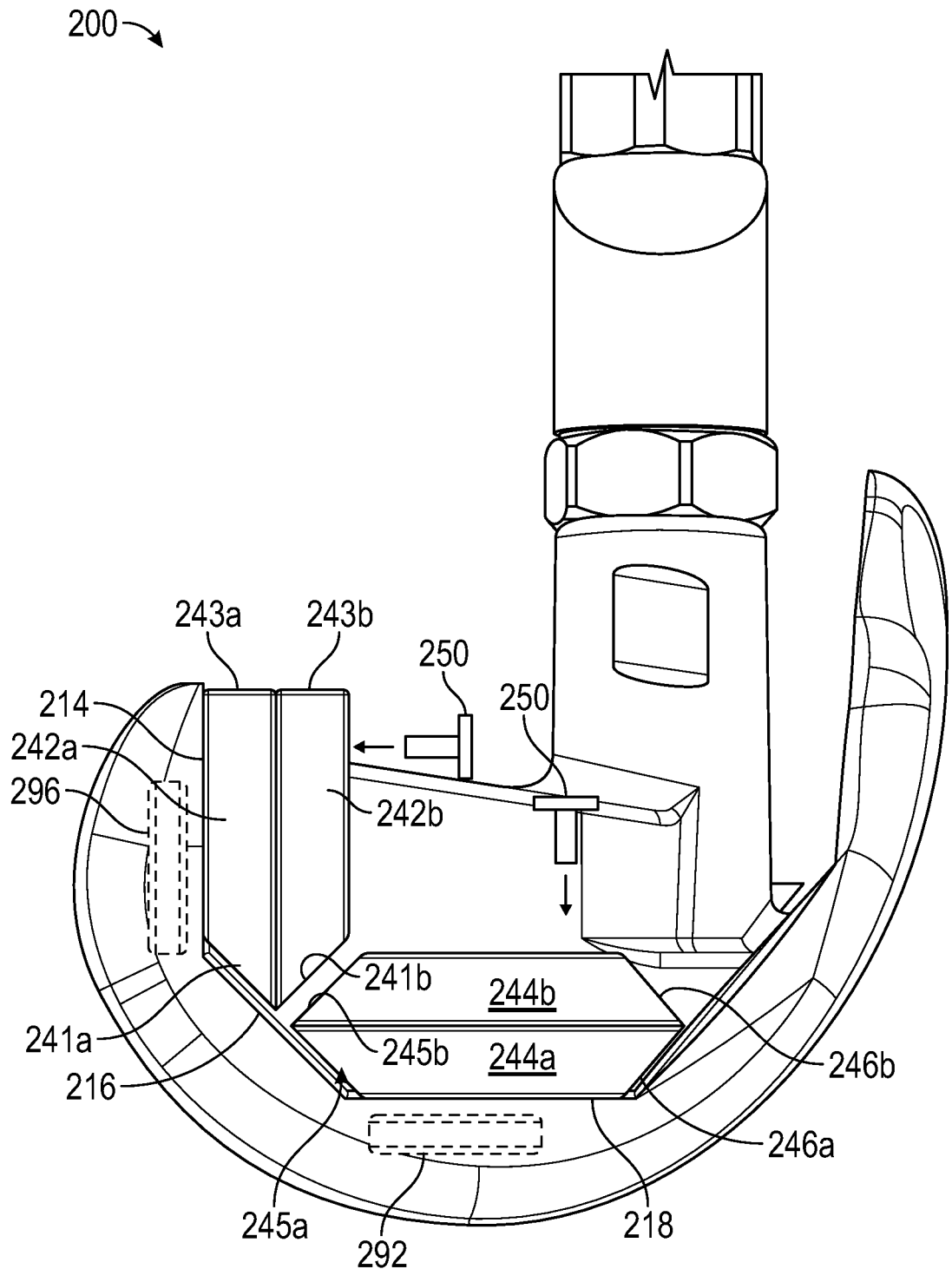
FIG. 3B shows the partial cutaway view of FIG. 3A further including additional spacers, each stacked on one of the spacers illustrated in FIG. 3A, in accordance with some embodiments.
Figure 3C:
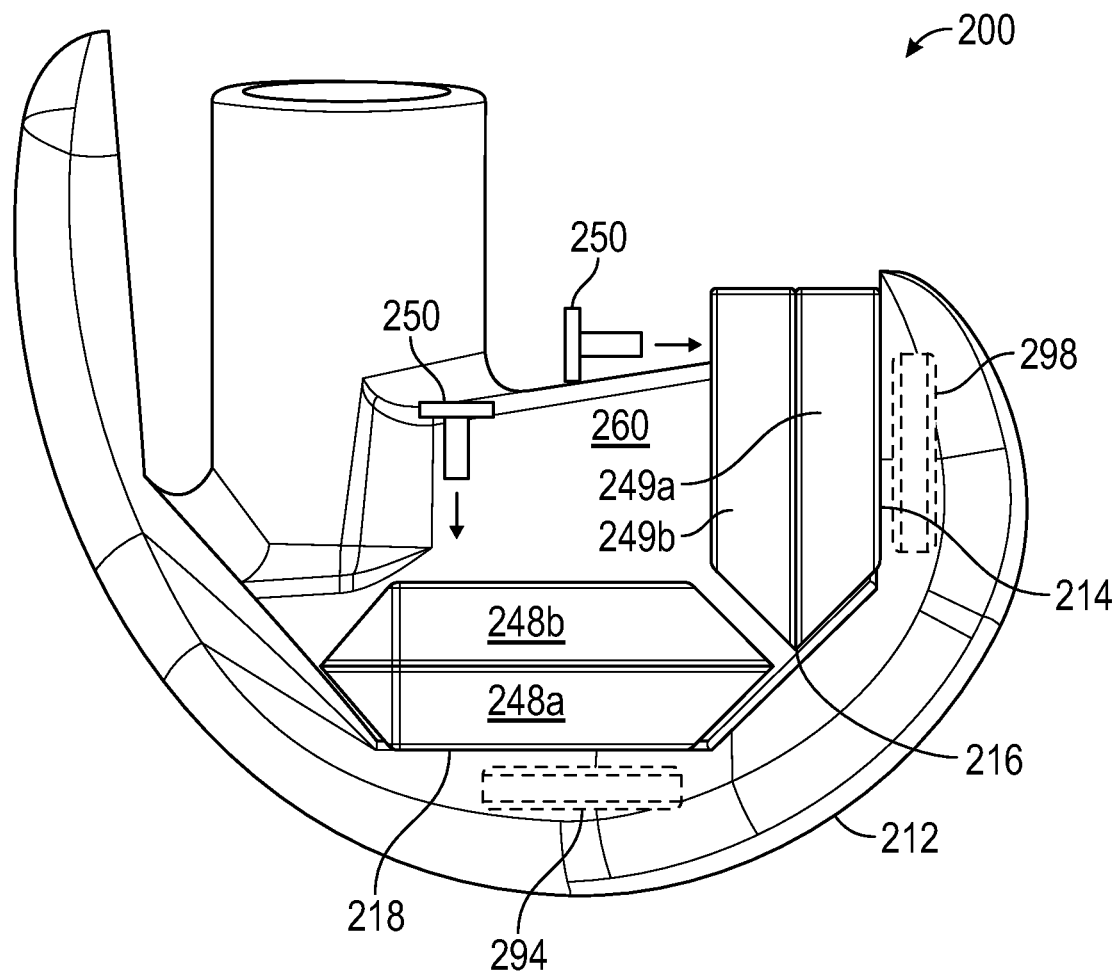
FIG. 3C shows a partial cutaway view of the distal femoral implant of FIG. 2 further including additional pairs of stacked spacers, as viewed from an opposite side of the distal femoral implant as FIGS. 2-3B, in accordance with some embodiments.

As illustrated in at least FIG. 3C, distal femoral implant 200 may further comprise at least one additional threaded aperture 294 configured to secure one or more stackable spacers to the portion of interior distal surface 218 disposed to an opposite side of median 260 from the portion in which threaded aperture 292 is disposed, utilizing a similar or same fastener 250. Likewise, distal femoral implant 200 may further comprise at least one additional threaded aperture 298 configured to secure one or more stackable spacers to the portion of interior posterior surface 214 disposed to an opposite side of median 260 from the portion in which threaded aperture 296 is disposed, utilizing a similar or same fastener 250.

Distal femoral implant 200 may further comprise one or more stackable spacers 242a, 242b, 244a, 244b, 248a, 248b, 249a, 249b. FIGS. 3A-3D show different partial cutaway views of distal femoral implant 200 of FIG. 2 including different configurations of such spacers 242a, 242b, 244a, 244b, 248a, 248b, 249a, 249b.

For example, a first posterior spacer 242a is configured to be secured directly to interior posterior surface 214 utilizing one or more screws 250 and a first distal spacer 244a is configured to be secured directly to interior distal surface 218 utilizing one or more screws 250, in accordance with some embodiments. First posterior spacer 242a and first distal spacer 244a are illustrated as being disposed on portions of interior posterior surface 214 and on portions of interior distal surface 218 that are each disposed to a first side of median 260.

FIG. 3B shows the partial cutaway view of distal femoral implant 200 of FIGS. 2 and 3A, further including a second posterior spacer 242b stacked in a flipped (e.g., mirrored) orientation and secured directly on first posterior spacer 242a utilizing one or more screws and a second distal spacer 244b stacked in a flipped (e.g., mirrored) orientation and secured directly on first distal spacer 244a utilizing one or more screws 250, in accordance with some embodiments.

In some embodiments, each of first and second posterior spacers 242a, 242b have a same shape, size and form factor. In some embodiments, each of first and second distal spacers 244a, 244b have a same shape, size and form factor. In yet other embodiments, all of first and second posterior spacers 242a, 242b and first and second distal spacers 244a, 244b have a same shape, size and form factor, for example as shown for first and second posterior spacers 242a, 242b or, for example as shown for first and second distal spacers 244a, 244b.

In some embodiments, opposing stackable surfaces of each of spacers 242a, 242b, 244a, 244b are substantially planar and parallel to one another such that, when stacked, negligible or no open space is present between mating stackable surfaces of adjacently stacked spacers.

In some embodiments, spacers 242a, 242b, 244a, 244b all have a same thickness (e.g., 5 mm, although any suitable thickness is also contemplated). In some embodiments, first and second posterior spacers 242a, 242b have a same first thickness, while first and second distal spacers 244a, 244b have a same second thickness. In yet other embodiments, one or more of spacers 242a, 242b, 244a, 244b have a different thickness (e.g., 7 mm, 8 mm or 10 mm, although any other suitable thickness is also contemplated) from one or more other of spacers 242a, 242b, 244a, 244b. By stacking one or more of posterior spacers 242a, 242b, having the same or different thicknesses, a greater variety of aggregate spacings between interior posterior surface 214 and a resected surface of a femur of the patient can be obtained compared to systems in which spacers are not specifically designed or configured to be so stacked. Similarly, by stacking one or more of distal spacers 244a, 244b, having the same or different thicknesses, a greater variety of aggregate spacings between interior distal surface 218 and a resected surface of a femur of the patient can be obtained compared to systems in which spacers are not specifically designed or configured to be so stacked. Moreover, stacking posterior spacers 242a, 242b or distal spacers 244a, 244b allows for a smaller total number of spacers to be utilized or inventoried while still providing an increased number of possible aggregate spacings at a lower cost of manufacture, use and/or inventory than is possible with other implant systems in which spacers are not specifically designed or configured to be so stacked.

As illustrated in FIGS. 3A and 3B, first and second posterior spacers 242a, 242b each include at least one respective beveled edge 241a, 241b having a bevel angle ($\theta_7$). In some embodiments, this bevel angle ($\theta_7$) is substantially equal to the second angle ($\theta_2$) between interior posterior surface 214 and interior intermediate surface 216, thereby allowing at least first posterior spacer 242a to simultaneously abut interior posterior surface 214 along its long surface and interior intermediate surface 216 along beveled edge 241a. However, any suitable bevel angle ($\theta_7$) is also contemplated. In some embodiments, first and second posterior spacers 242a, 242b each include an edge 243a, 243b opposite beveled edge 241a, 241b disposed perpendicular to the direction of extension of their long surfaces.

As illustrated in FIGS. 3A and 3B, first and second distal spacers 244a, 244b each include respective opposing beveled edges 245a, 245b having respective bevel angle ($\theta_9$) and 246a, 246b having respective bevel angle ($\theta_{10}$). In some embodiments, bevel angle ($\theta_9$) is substantially equal to the third angle ($\theta_3$) between interior intermediate surface 216 and interior distal surface 218, thereby allowing at least first distal spacer 244a to simultaneously abut interior distal surface 218 along its long surface and interior intermediate surface 216 along beveled edge 245a. However, any suitable bevel angle ($\theta_9$) is also contemplated. In some embodiments, bevel angle ($\theta_{10}$) is substantially equal to the sixth angle ($\theta_6$) between interior distal surface 218 and second interior intermediate surface 217, thereby allowing at least first distal spacer 244a to simultaneously abut interior distal surface 218 along its long surface and interior intermediate surface 216 along beveled edge 246a. However, any suitable bevel angle ($\theta_{10}$) is also contemplated.

As illustrated in FIG. 3B, second posterior spacer 242b is configured to be stacked directly on and in a flipped (e.g., mirrored) orientation compared to first posterior spacer 242a such that respective beveled edges 241a, 241b of first and second posterior spacers 242a, 242b meet at a common point. Similarly, second distal spacer 244b is configured to be stacked directly on and in a flipped (e.g., mirrored) orientation compared to first distal spacer 244a such that respective beveled edges 245a, 245b meet at a first common point and respective beveled edges 246a, 246b meet at a second common point.

Embodiments where all of angles ($\theta_2$, $\theta_3$, $\theta_6$, $\theta_7$, $\theta_9$, and $\theta_{10}$) are substantially 45° also allow for simultaneous stacking of at least 2 posterior spacers on interior posterior surface 214 and at least 2 distal spacers on interior distal surface 218, in some but not necessarily all such embodiments, with negligible or substantially no space between adjacent mating surfaces of the spacers, since beveled edge 241*b* of second posterior spacer 242*b* and beveled edge 245*b* of second distal spacer 244*b* align substantially parallel and adjacent to one another (see FIG. 3B).

FIG. 3C illustrates a partial cutaway view of distal femoral implant 200 of FIG. 2 as viewed from the opposite side of median 260 from the view of FIGS. 2-3B. Threaded apertures 294 and 298 are substantially identical to respective threaded apertures 292 and 296, being configured to receive similar or identical fasteners 250 but disposed within portions of their respective surfaces disposed to an opposite side of median 260. FIG. 3C similarly illustrates spacers 248*a* and 248*b*, which are substantially identical to respective spacers 244*a*, 244*b* except being disposed or disposable an opposite side of median 260. FIG. 3C similarly illustrates spacers 249*a* and 249*b*, which are substantially identical to respective spacers 242*a*, 242*b* except being disposed or disposable an opposite side of median 260.

Figure 3D:
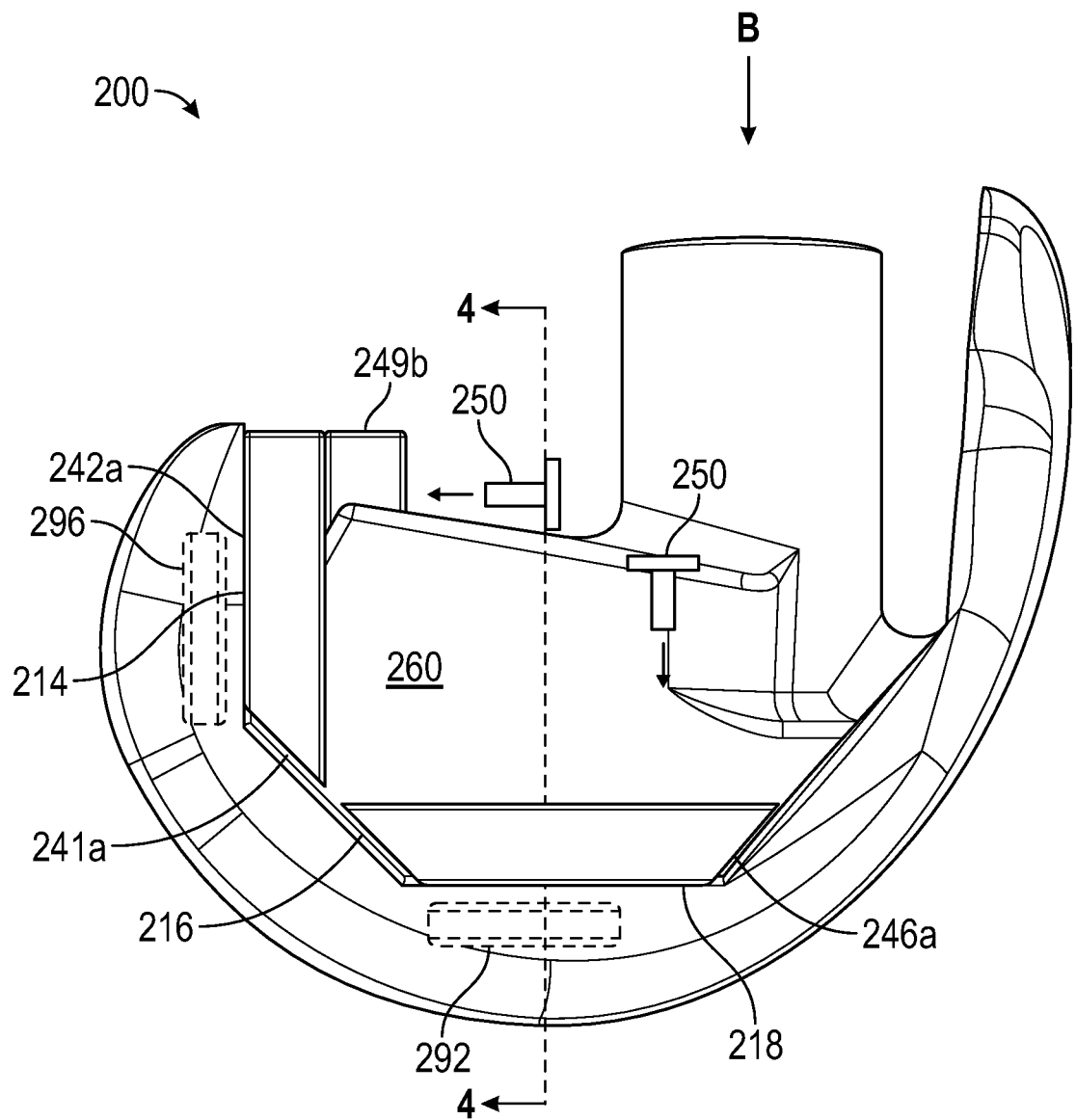
FIG. 3D shows the partial cutaway view of FIG. 3A and further including the additional pairs of stacked spacers of FIG. 3C, in accordance with some embodiments.

For ease of visualization and understanding, FIG. 3D illustrates the partial cutaway view of distal femoral implant 200 shown in FIGS. 2 and 3A, however, further comprising spacers 248*a*, 248*b*, 249*a*, 249*b*. Of course, in FIG. 3D the view of spacer 249*a* is obstructed by spacer 242*a* and median 260, the view of spacer 249*b* is partially obstructed by median 260, and the view of spacers 248*a*, 248*b* is entirely obstructed by median 260.

Figure 4:
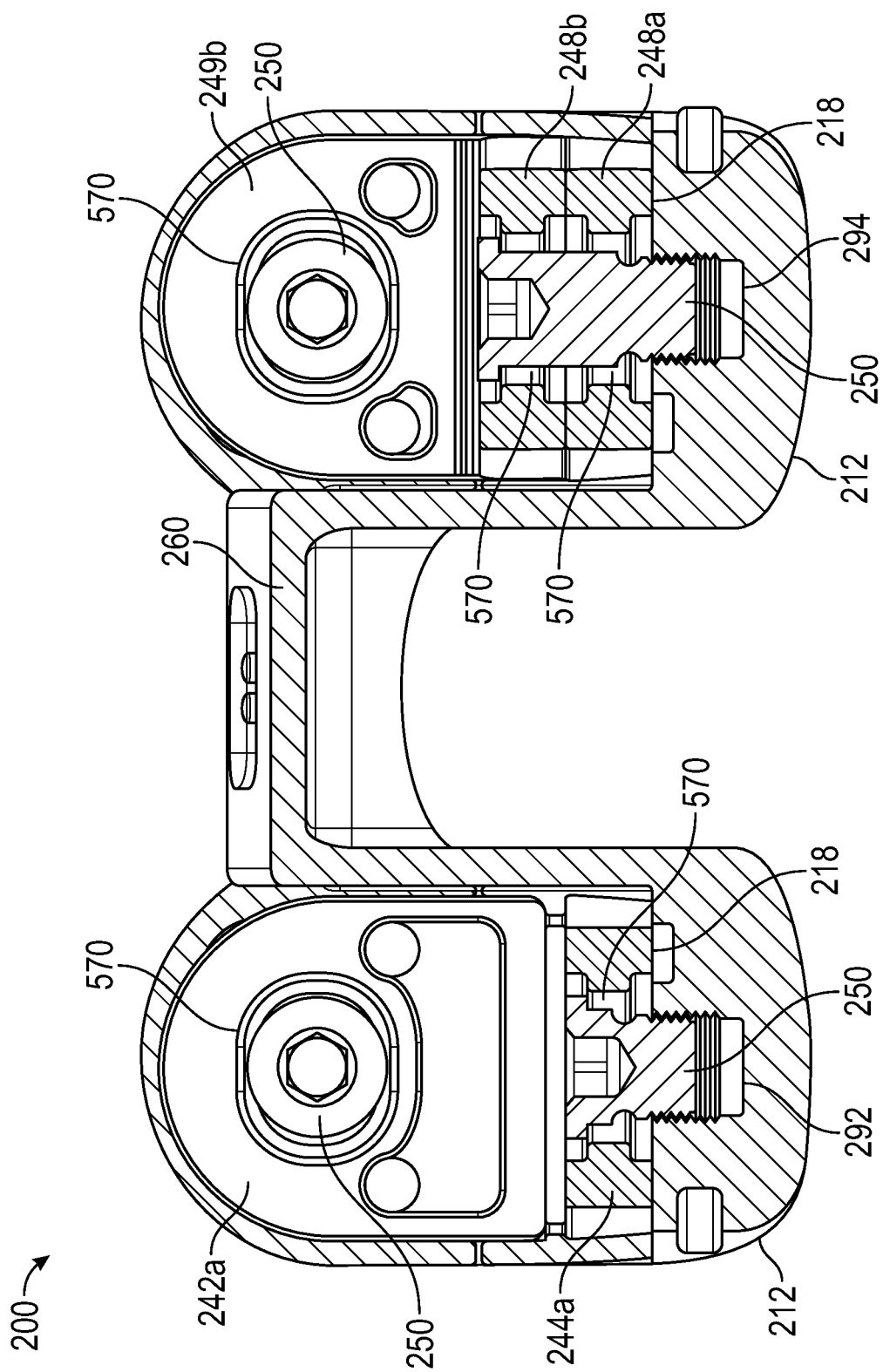
FIG. 4 shows a cutaway view of the distal femoral implant of FIG. 3D as viewed along the cutline 4 and in the direction of the cutline arrows illustrated in FIG. 3D, in accordance with some embodiments.

FIG. 4 illustrates a cutaway view of distal femoral implant 200 as shown in FIG. 3D but viewed along the cut line 4 and in the direction of the cut-line arrows, in accordance with some embodiments. As illustrated, one or more (e.g., each) of spacers 242*a* (and 242*b*), 244*a* (and 244*b*), 248*a*, 248*b*, 249*a*, 249*b* comprises a slot 570 having a substantially larger lateral dimension than an anterior-posterior dimension. Slot 570 is configured to receive a respective fastener 250. The larger lateral dimension of slot 570 compared to its anterior-posterior dimension allows a user and/or surgeon to adjust the medial/lateral position of the spacer(s) with respect to fasteners 250 and, so also, with respect to distal femoral implant 200, any of its features, and/or any bone deficiencies. This allows the surgeon to optimize the placement of the spacers depending on those bone deficiencies to maximize coverage.

Figure 5:
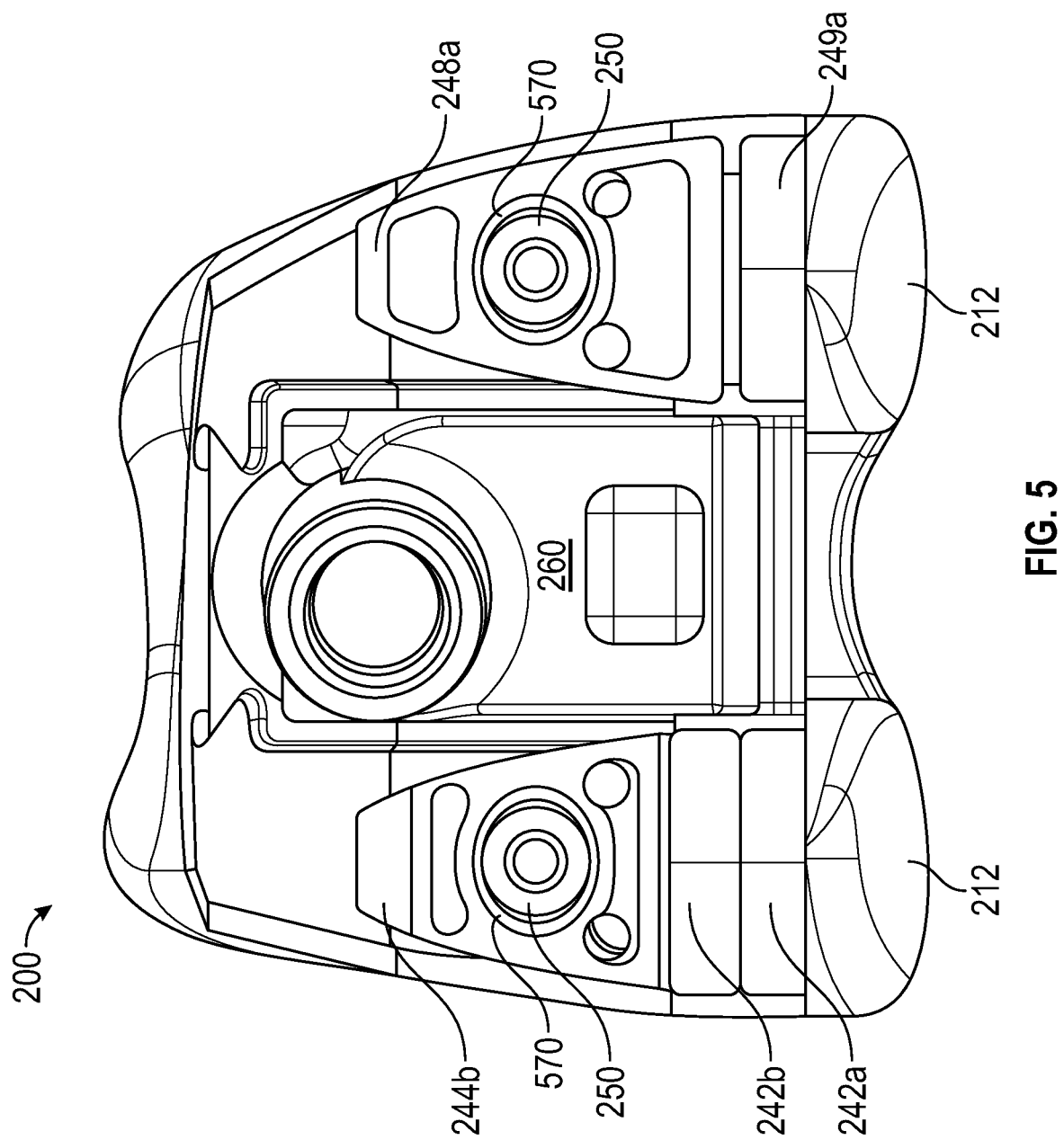
FIG. 5 shows a top view of the distal femoral implant of any of FIGS. 2-4 as viewed in the direction of arrow B illustrated in FIG. 3D, in accordance with some embodiments.

FIG. 5 illustrates a top view of distal femoral implant 200 as viewed in the direction of arrow B, for example, in FIG. 3D, in accordance with some embodiments. FIG. 5 provides another view of slots 570 of each of the spacers, of median 260, and of various features of distal femoral implant 200.

Discussion will now turn to example methods for using one or both of tibial baseplate implant 100, for example as described in connection with at least FIG. 1, and distal femoral implant 200, for example as described in connection with at least any one or more of FIGS. 2-5 above.

Figure 6:
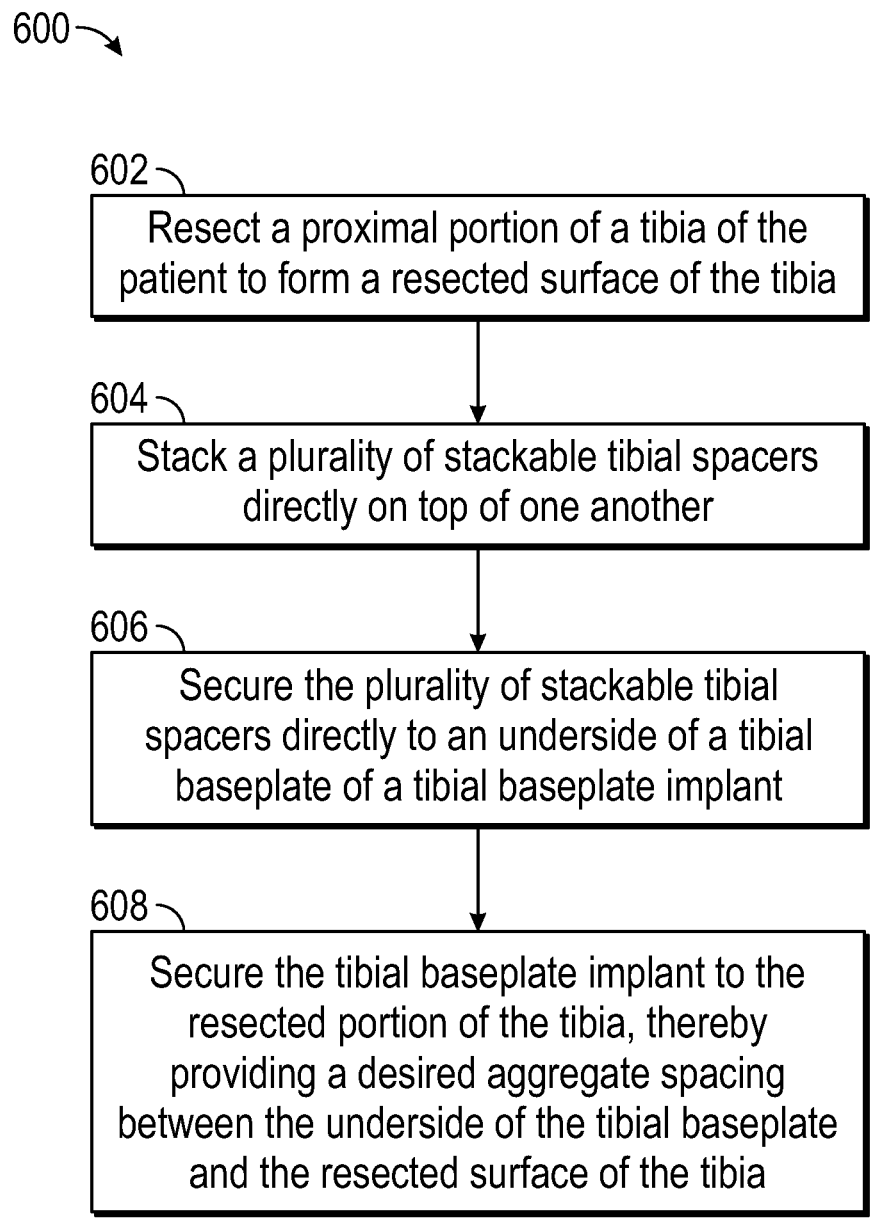
FIG. 6 shows a flowchart relating to a method for using a tibial baseplate implant, in accordance with some embodiments.

FIG. 6 shows a flowchart 600 relating to a method for using at least a tibial baseplate implant, in accordance with some embodiments. Such methods comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Turning to flowchart 600, block 602 includes resecting a proximal portion of a tibia of the patient to form a resected surface of the tibia.

Block 604 includes stacking a plurality of stackable tibial spacers directly on top of one another. For example, as previously described in connection with at least FIG. 1, plurality of spacers, e.g., 140*b*, 140*c*, can be stacked directly against, or on top of, one another. In some embodiments, plurality of stackable tibial spacers 140*a*-140*c* are one of substantially circular shaped and substantially semi-circular shaped. In some embodiments, each of stackable tibial spacers 140*a*-140*c* have a same thickness (e.g., 6 mm). In some other embodiments, at least one of stackable tibial spacers 140*a*-140*c* has a first thickness and at least one other of the plurality of stackable tibial spacers 140*a*-140*c* has a second thickness different from the first thickness.

Block 606 includes securing the plurality of stackable tibial spacers directly to an underside of a tibial baseplate of a tibial baseplate implant. For example, as previously described in connection with at least FIG. 1, plurality of spacers, e.g., 140*b*, 140*c* and in some cases 140*a*, can be secured directly to underside 114 of tibial baseplate 110 of a tibial baseplate implant 100. In some embodiments, plurality of stackable tibial spacers 140*a*-140*c* are configured to be secured to underside 114 of tibial base plate 110 utilizing one or more screws 250.

Block 608 includes securing the tibial baseplate implant to the resected portion of the tibia, thereby providing a desired aggregate spacing between the underside of the tibial baseplate and the resected surface of the tibia. For example, as previously described in connection with at least FIG. 1, tibial baseplate implant 100 can be secured to the resected portion of the tibia of the patient, thereby providing a desired aggregate spacing between underside 114 of tibial baseplate 110 and the resected surface of the tibia.

In some embodiments, tibial baseplate implant 100 further includes distal transitional portion 120 coupled to underside 114 of tibial baseplate 110, and stem 130 coupled to distal transitional portion 120. Stem 130 is configured to be disposed within a cavity of the tibia of the patient. In some embodiments, stem 130 has a substantially cylindrical shape, a distal end that tapers to a point, and one or more longitudinal grooves 132*a*-132*c* configured to aid adhesion of stem 130 to a surface of the tibia of the patient.

In some embodiments, distal transitional portion 120 tapers from a proximal end toward a distal end and includes one or more protrusions that extend laterally away from distal transitional portion 120. Such one or more protrusions are configured to aid in at least one of adhesion of distal transition portion 120 to a surface of the tibia of the patient and/or aligning plurality of stackable tibial spacers, e.g., 140*b*, 140*c* and in some cases 140*a*, on underside 114 of tibial baseplate 110.

Figure 7:
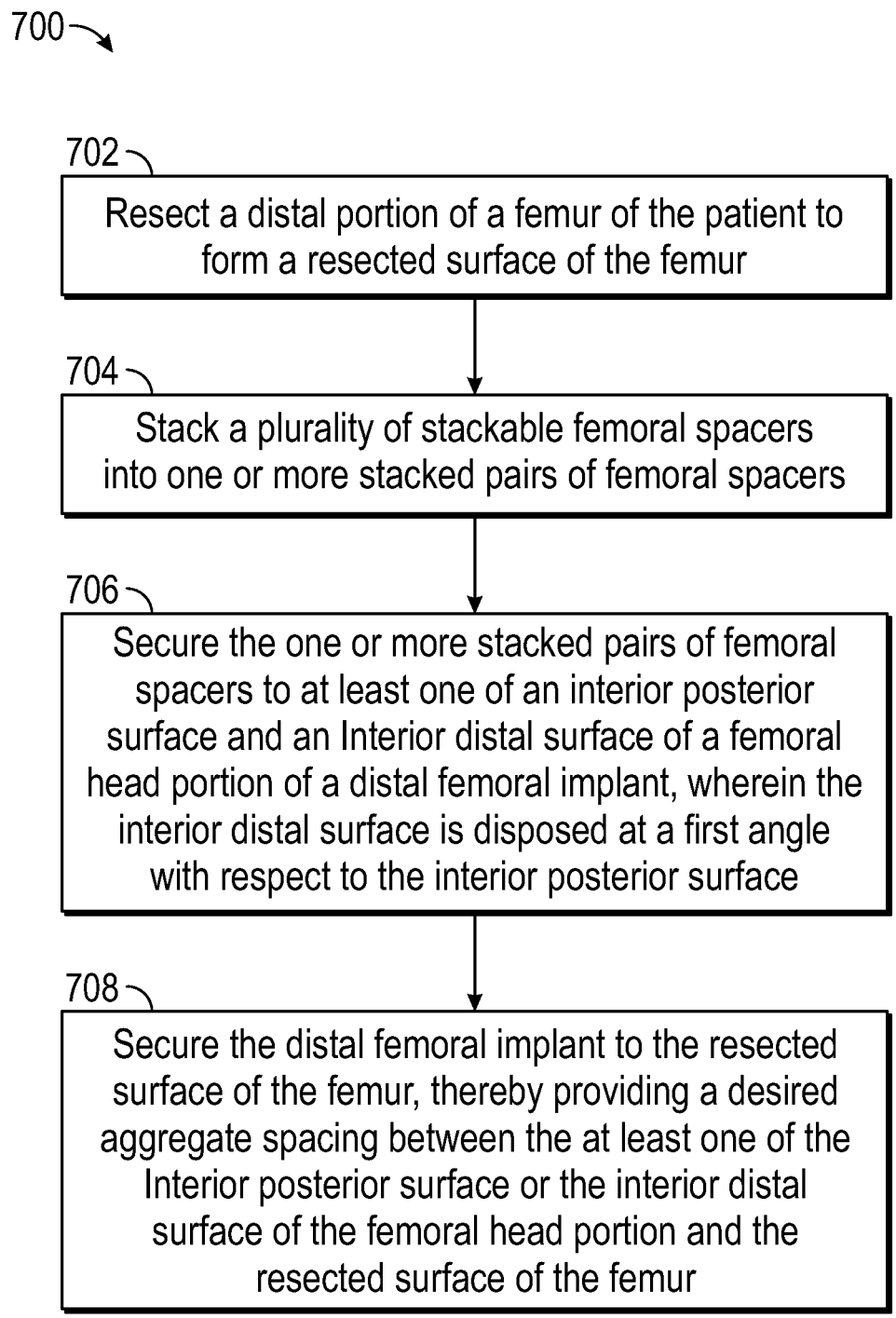
FIG. 7 shows another flowchart relating to a method for using a distal femoral implant, in accordance with some embodiments.

FIG. 7 shows another flowchart 700 relating to a method for using at least a distal femoral implant, in accordance with some embodiments. Such methods comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Turning to flowchart 700, block 702 includes resecting a distal portion of a femur of the patient to form a resected surface of the femur.

Block 704 includes stacking a plurality of stackable femoral spacers into one or more stacked pairs of femoral spacers. For example, as previously described in connection with one or more of FIGS. 3B-5, posterior spacers 242a, 242b can be stacked directly on one another, distal spacers 244a, 244b can be stacked directly on one another, posterior spacers 249a, 249b can be stacked directly on one another, and/or distal spacers 248a, 248b can be stacked directly on one another.

In some embodiments, stacking the plurality of stackable femoral spacers comprises disposing first posterior spacer 242a directly against interior posterior surface 214 and disposing second posterior spacer 242b directly against, and in a mirrored orientation with respect to, first posterior spacer 242a such that the respective first beveled edges 241a, 241b of first and second posterior spacers 242a, 242b meet at a first common point.

In some embodiments, stacking the plurality of stackable femoral spacers further and/or alternatively includes disposing first distal spacer 244a directly against interior distal surface 218, and disposing second distal spacer 244b directly against, and in a mirrored orientation with respect to, first distal spacer 244a such that the respective first beveled edges 245a, 245b of first and second distal spacers 244a, 244b meet at a second common point.

In some embodiments, stacking the plurality of stackable femoral spacers comprises disposing third posterior spacer 249a directly against a portion of interior posterior surface 214 to a side of median 260 opposite a portion of interior posterior surface 214 against which first posterior spacer 242a may be disposed, and disposing fourth posterior spacer 249b directly against, and in a mirrored orientation with respect to, third posterior spacer 249a such that the respective first beveled edges 241a, 241b of third and fourth posterior spacers 249a, 249b meet at a third common point.

In some embodiments, stacking the plurality of stackable femoral spacers further and/or alternatively includes disposing third distal spacer 248a directly against a portion of interior distal surface 218 to a side of median 260 opposite a portion of interior distal surface 218 against which first distal spacer 244a may be disposed, and disposing fourth distal spacer 248b directly against, and in a mirrored orientation with respect to, third distal spacer 248a such that the respective first beveled edges 245a, 245b of third and fourth distal spacers 244a, 244b meet at a fourth common point.

In some embodiments, each of femoral spacers 242a, 242b, 244a, 244b, 248a, 248b, 249a, 249b have a same thickness (e.g., 5 mm). In some other embodiments, at least one of spacers 242a, 242b, 244a, 244b, 248a, 248b, 249a, 249b has a first thickness and at least one other of spacers 242a, 242b, 244a, 244b, 248a, 248b, 249a, 249b has a second thickness different from the first thickness.

Block 706 includes securing the one or more stacked pairs of femoral spacers to at least one of an interior posterior surface and an interior distal surface of a femoral head portion of a distal femoral implant, wherein the interior distal surface is disposed at a first angle with respect to the interior posterior surface. For example, as previously described in connection with at least FIG. 4, posterior spacers 242a, 242b and/or 249a, 249b can be secured to respective portions of interior posterior surface 214 utilizing one or more screws 250 and/or distal spacers 244a, 244b and/or 248a, 248b can be secured to interior distal surface 218 of femoral head portion 210 of distal femoral implant 200 utilizing one or more screws 250.

In some embodiments, securing the plurality of stackable femoral spacers to least one of an interior posterior surface and an interior distal surface of a femoral head portion of a distal femoral implant comprises securing a screw through respective slots in stacked pairs of the stackable femoral spacers, each of the respective slots having a substantially larger lateral dimension than an anterior-posterior dimension that allows for adjustment of a medial/lateral position of each of the spacer with respect to distal femoral implant 200.

As described in connection with FIGS. 2-5, interior distal surface 218 is disposed at a first angle ($\theta_1$) with respect to interior posterior surface 214. Femoral head portion 210 further includes outer arcuate surface 212, which is configured to mate with one of tibial baseplate 110 or a proximal surface of a tibia of the patient. Femoral head portion 210 further includes first interior intermediate surface 2116 joining interior posterior surface 214 and interior distal surface 218. First interior intermediate surface 216 is disposed at a second angle ($\theta_2$) with respect to interior posterior surface 214 and at a third angle ($\theta_3$) with respect to interior distal surface 218. In some embodiments, the second angle ($\theta_2$) is substantially equal to the third angle ($\theta_3$). And in some such embodiments, that angle is 45°.

In some embodiments, femoral head portion 210 further includes interior anterior surface 219 disposed at a fourth angle ($\theta_4$) with respect to interior distal surface 218 and second interior intermediate surface 217 joining interior anterior surface 219 and interior distal surface 218. Second interior intermediate surface 170 is disposed at a fifth angle ($\theta_5$) with respect to interior anterior surface 219 and at a sixth angle ($\theta_6$) with respect to interior distal surface 218. In some embodiments, the sixth angle ($\theta_6$) between interior distal surface 218 and second interior intermediate surface 217 is substantially equal to the third angle ($\theta_3$) between interior distal surface 218 and first interior intermediate surface 216.

In some embodiments, interior posterior surface 214, interior distal surface 218 and first interior intermediate surface 216 are each substantially planar. In some embodiments, each of plurality of stackable femoral spacers 242a, 242b, 244a, 244b, 248a, 248b, 249a, 249b include at least a respective first beveled edge (e.g., 241a for spacers 242a and/or 249a; 241b for spacers 242b and/or 249b; 245a for spacers 244a and/or 248a; 245b for spacers 244b and/or 248b). In some embodiments, this first respective beveled edge has a bevel angle of substantially 45°. In some embodiments, each of first through fourth distal spacers 244a, 244b, 248a, 248b include a respective second beveled edge (e.g., 246a for spacers 244a and/or 248a and 246b for spacers 244b and/or 248b) such that, when stacked, the respective second beveled edges 246a, 246b of first and second distal spacers 244a, 244b meet at a third common point and/or such that, when stacked, the respective second beveled edges 246a, 246b of third and fourth distal spacers 248a, 248b meet at a fourth common point. In some embodiments, this second respective beveled edge has a bevel angle of substantially 45°.

In some embodiments, for example as illustrated in FIGS. 3B-5, when secured, first beveled edge 245b of second posterior spacer 244b is substantially parallel to, and disposed immediately adjacent to, first beveled edge 241b of second distal spacer 242b. In some similar or same embodiments, when secured, first beveled edge 245b of fourth posterior spacer 249b is substantially parallel to, and disposed immediately adjacent to, first beveled edge 241b of fourth distal spacer 248b.

Block 708 includes securing the distal femoral implant to the resected surface of the femur, thereby providing a desired aggregate spacing between the at least one of the interior posterior surface or the interior distal surface of the femoral head portion and the resected surface of the femur. For example, as previously described in connection with at least FIG. 2-5, distal femoral implant 200 can be secured to the resected surface of the femur, thereby providing a desired aggregate spacing between at least one of interior posterior surface 214 or interior distal surface 218 of femoral head portion 210 and the resected surface of the femur.

Various aspects of the novel systems, apparatuses, and methods are described more fully hereinafter with reference to the accompanying drawings. The teachings disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the novel systems, apparatuses, and methods disclosed herein, whether implemented independently of or combined with any other aspect of the disclosure. For example, a system or an apparatus may be implemented, or a method may be practiced using any one or more of the aspects set forth herein. In addition, the scope of the disclosure is intended to cover such a system, apparatus or method which is practiced using other structure, functionality, or structure and functionality in addition to or other than the various aspects of the disclosure set forth herein. It should be understood that any aspect disclosed herein may be set forth in one or more elements of a claim. Although some benefits and advantages of the preferred aspects are mentioned, the scope of the disclosure is not intended to be limited to particular benefits, uses, or objectives. The detailed description and drawings are merely illustrative of the disclosure rather than limiting, the scope of the disclosure being defined by the appended claims and equivalents thereof.

General Interpretive Principles for the Present Disclosure

Various aspects of the novel systems, apparatuses, and methods are described more fully hereinafter with reference to the accompanying drawings. The teachings disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the novel systems, apparatuses, and methods disclosed herein, whether implemented independently of or combined with any other aspect of the disclosure. For example, a system or an apparatus may be implemented, or a method may be practiced using any one or more of the aspects set forth herein. In addition, the scope of the disclosure is intended to cover such a system, apparatus or method which is practiced using other structure, functionality, or structure and functionality in addition to or other than the various aspects of the disclosure set forth herein. It should be understood that any aspect disclosed herein may be set forth in one or more elements of a claim. Although some benefits and advantages of the preferred aspects are mentioned, the scope of the disclosure is not intended to be limited to particular benefits, uses, or objectives. The detailed description and drawings are merely illustrative of the disclosure rather than limiting, the scope of the disclosure being defined by the appended claims and equivalents thereof.

The use of the anatomical term "distal" is understood by those having skill in the art and can be understood to describe a location with respect to a center of a patient's body. For example, a distal femur would be located substantially at or near the distant or far end of the femur from its connection to the hip.

The use of the anatomical term "proximal" is understood by those having skill in the art and can be understood to describe a location with respect to a center of a patient's body. For example, a proximal tibia would be located substantially at or near the proximate or closest end of the tibia to the femur.

The use of the anatomical term "posterior" is understood by those having skill in the art and can be understood to describe a location toward the back side of the feature being descriptively modified with respect to a plane, for example, running from head to toe of a patient. For example, a posterior surface would be understood to be located toward a back side of the feature with respect to a plane, for example, running from head to toe of a patient.

The use of the anatomical term "anterior" is understood by those having skill in the art and can be understood to be substantially opposite of "posterior," describing a location toward the front side of the feature being descriptively modified with respect to a plane, for example, running from head to toe of a patient. For example, an anterior surface would be understood to be located toward a front side of the feature with respect to a plane, for example, running from head to toe of a patient.

With respect to the use of plural vs. singular terms herein, those having skill in the art can translate from the plural to the singular and/or from the singular to the plural as is appropriate to the context and/or application. The various singular/plural permutations may be expressly set forth herein for sake of clarity.

When describing an absolute value of a characteristic or property of a thing or act described herein, the terms "substantial," "substantially," "essentially," "approximately," and/or other terms or phrases of degree may be used without the specific recitation of a numerical range. When applied to a characteristic or property of a thing or act described herein, these terms refer to a range of the characteristic or property that is consistent with providing a desired function associated with that characteristic or property. For example, the terms "approximately," "about" and "substantially" may refer to an amount that is within less than 10% of, within less than 5% of, within less than 1% of, within less than 0.1% of, and within less than 0.01% of the stated amount.

In those cases where a single numerical value is given for a characteristic or property, it is intended to be interpreted as at least covering deviations of that value within one significant digit of the numerical value given.

If a numerical value or range of numerical values is provided to define a characteristic or property of a thing or act described herein, whether or not the value or range is qualified with a term of degree, a specific method of measuring the characteristic or property may be defined herein as well. In the event no specific method of measuring the characteristic or property is defined herein, and there are different generally accepted methods of measurement for the characteristic or property, then the measurement method should be interpreted as the method of measurement that would most likely be adopted by one of ordinary skill in the art given the description and context of the characteristic or property. In the further event there is more than one method of measurement that is equally likely to be adopted by one of ordinary skill in the art to measure the characteristic or property, the value or range of values should be interpreted as being met regardless of which method of measurement is chosen.

It will be understood by those within the art that terms used herein, and especially in the appended claims (e.g., bodies of the appended claims) are intended as "open" terms unless specifically indicated otherwise (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

In those instances where a convention analogous to "at least one of A, B, and C" is used, such a construction would include systems that have A alone, B alone, C alone, A and B together without C, A and C together without B, B and C together without A, as well as A, B, and C together. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include A without B, B without A, as well as A and B together."

Various modifications to the implementations described in this disclosure can be readily apparent to those skilled in the art, and generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "exemplary" is used exclusively herein to mean "serving as an example, instance, or illustration." Any implementation described herein as "exemplary" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

What is claimed is:

1. A knee replacement prosthesis for a patient, comprising:
    a distal femoral implant comprising:
        a femoral head portion comprising:
            an outer arcuate surface configured to mate with one of a tibial baseplate or a proximal surface of a tibia of the patient;
            an interior posterior surface;
            an interior distal surface disposed at a first angle with respect to the interior posterior surface; and
            a first interior intermediate surface joining the interior posterior surface and the interior distal surface, the first interior intermediate surface disposed at a second angle with respect to the interior posterior surface and at a third angle with respect to the interior distal surface; and
        a plurality of stackable femoral spacers, each comprising a respective first beveled edge, wherein:
            a first posterior spacer of the plurality of stackable femoral spacers is disposed directly against the interior posterior surface; and
            a second posterior spacer of the plurality of stackable femoral spacers is disposed directly against, and in a mirrored orientation with respect to, the first posterior spacer such that the respective first beveled edges of the first and second posterior spacers meet at a first common point.

2. The prosthesis of claim 1, wherein each of the plurality of stackable femoral spacers comprises a slot configured to receive a fastener to, thereby, secure the respective femoral spacer to at least one of: another of the stackable femoral spacers, the interior posterior surface and the interior distal surface of the distal femoral implant, the slot comprising a substantially larger lateral dimension than an anterior-posterior dimension, thereby allowing lateral adjustment of a secured position of the respective femoral spacer with respect to the distal femoral implant.

3. The prosthesis of claim 1, wherein the interior posterior surface, the interior distal surface and the first interior intermediate surface are each substantially planar.

4. The prosthesis of claim 1, wherein the second angle is substantially equal to the third angle.

5. The prosthesis of claim 4, wherein the second angle and the third angle are each substantially equal to 45°.

6. The prosthesis of claim 1, wherein the respective first beveled edges each have an angle of substantially 45°.

7. The prosthesis of claim 1, wherein the distal femoral implant comprises a median and the plurality of stackable femoral spacers further comprises:
    a third posterior spacer disposed directly against a portion of the interior posterior surface disposed to an opposite side of the median from the first posterior spacer; and
    a fourth posterior spacer disposed directly against, and in a mirrored orientation with respect to, the third posterior spacer such that the respective first beveled edges of the third and fourth posterior spacers meet at a third common point.

8. The prosthesis of claim 1, wherein the plurality of stackable femoral spacers further comprises:
   a first distal spacer disposed directly against the interior distal surface; and
   a second distal spacer disposed directly against, and in a mirrored orientation with respect to, the first distal spacer such that the respective first beveled edged the first and second distal spacers meet at a second common point.

9. The prosthesis of claim 8, wherein the distal femoral implant comprises a median and the plurality of stackable femoral spacers further comprises:
   a third distal spacer disposed directly against a portion of the interior distal surface disposed to an opposite side of the median from the first distal spacer; and
   a fourth distal spacer disposed directly against, and in a mirrored orientation with respect to, the third distal spacer such that the respective first beveled edges the third and fourth distal spacers meet at a third common point.

10. The prosthesis of claim 8, wherein the first beveled edge of the second posterior spacer is substantially parallel to, and disposed immediately adjacent to, the first beveled edge of the second distal spacer.

11. The prosthesis of claim 10, wherein the respective second beveled edges have an angle of substantially 45°.

12. The prosthesis of claim 8, wherein each of the first and second distal spacers comprise a respective second beveled edge such that the respective second beveled edges of the first and second distal spacers meet at a third common point.

13. The prosthesis of claim 1, wherein each of the plurality of stackable femoral spacers has a same thickness.

14. The prosthesis of claim 1, wherein at least one of the plurality of stackable femoral spacers has a first thickness and at least one other of the plurality of stackable femoral spacers has a second thickness different from the first thickness.

15. The prosthesis of claim 14, wherein the sixth angle between the interior distal surface and the second interior intermediate surface is substantially equal to the third angle between the interior distal surface and the first interior intermediate surface.

16. The prosthesis of claim 1, wherein the femoral head portion further comprises:
   an interior anterior surface disposed at a fourth angle with respect to the interior distal surface; and
   a second interior intermediate surface joining the interior anterior surface and the interior distal surface, the second interior intermediate surface disposed at a fifth angle with respect to the interior anterior surface and at a sixth angle with respect to the interior distal surface.

* * * * *